(12) United States Patent
Choi et al.

(10) Patent No.: US 10,739,827 B2
(45) Date of Patent: Aug. 11, 2020

(54) SUPPORTING DEVICE FOR DISPLAY DEVICE

(71) Applicant: SAMSUNG MEDISON CO., LTD., Gangwon-do (KR)

(72) Inventors: Won Jun Choi, Hwaseong-si (KR); Jae Wook Lee, Seoul (KR)

(73) Assignee: SAMSUNG MEDISON CO. LTD., Hongcheon-gun, Ganwon-do (KR)

( * ) Notice: Subject to any disclaimer, the term of this patent is extended or adjusted under 35 U.S.C. 154(b) by 25 days.

(21) Appl. No.: 16/242,324

(22) Filed: Jan. 8, 2019

(65) Prior Publication Data

US 2019/0212785 A1    Jul. 11, 2019

(30) Foreign Application Priority Data

Jan. 8, 2018    (KR) ........................ 10-2018-0002427

(51) Int. Cl.
| | |
|---|---|
| *G06F 1/16* | (2006.01) |
| *A61B 6/00* | (2006.01) |
| *F16M 11/00* | (2006.01) |
| *F16M 11/12* | (2006.01) |

(52) U.S. Cl.
CPC ............ *G06F 1/1681* (2013.01); *A61B 6/462* (2013.01); *F16M 11/00* (2013.01); *F16M 11/125* (2013.01); *G06F 1/1601* (2013.01); *G06F 1/1622* (2013.01)

(58) Field of Classification Search
CPC .... G06F 1/1601; G06F 1/1622; G06F 1/1681; A61B 6/462; F16M 11/00; F16M 11/125
See application file for complete search history.

(56) References Cited

U.S. PATENT DOCUMENTS

| | | | | |
|---|---|---|---|---|
| 4,691,886 A | * | 9/1987 | Wendling ............... | F16M 11/10 248/123.11 |
| 4,953,822 A | * | 9/1990 | Sharber .............. | F16M 11/2014 248/280.11 |
| 5,037,053 A | * | 8/1991 | Fox ....................... | A47F 5/0876 248/280.11 |

(Continued)

FOREIGN PATENT DOCUMENTS

| | | |
|---|---|---|
| EP | 1 855 045 A1 | 11/2007 |
| JP | 2009-082275 A | 4/2009 |

(Continued)

OTHER PUBLICATIONS

Extended Search Report issued in corresponding European Application No. 19150095.8, dated Jun. 5, 2019.

*Primary Examiner* — Adrian S Wilson
(74) *Attorney, Agent, or Firm* — Morgan Lewis & Bockius LLP

(57) ABSTRACT

Disclosed is a supporting device for a display device displaying an image, which includes a multi-joint arm including at least one joint, a hinge connected to one end of the multi-joint arm and rotatably coupled with the display device about a rotation axis extending in the front-rear direction of the display device, a damper to restrict rotation of the hinge to a certain extent to shorten a rotation time of the hinge when the hinge is rotated, and a brake to fix the hinge when the rotation of the hinge is finished, wherein the hinge is disposed on the same plane as the center of gravity of the display device in a vertical direction of the display device.

20 Claims, 13 Drawing Sheets

(56) References Cited

U.S. PATENT DOCUMENTS

| | | | | |
|---|---|---|---|---|
| 5,566,048 A | * | 10/1996 | Esterberg | G06F 1/1616 16/307 |
| 5,842,672 A | * | 12/1998 | Sweere | A47B 21/00 248/278.1 |
| 6,019,332 A | | 2/2000 | Sweere et al. | |
| 6,543,734 B2 | * | 4/2003 | Yeh | F16M 11/10 248/291.1 |
| 7,028,961 B1 | * | 4/2006 | Dittmer | F16M 11/04 248/278.1 |
| 2006/0186295 A1 | | 8/2006 | Dittmer et al. | |
| 2010/0193647 A1 | | 8/2010 | Huang et al. | |
| 2016/0319986 A1 | | 11/2016 | Hörndler | |

FOREIGN PATENT DOCUMENTS

| | | |
|---|---|---|
| JP | 2016-501097 A | 1/2016 |
| KR | 10-2016-0013434 A | 2/2016 |

\* cited by examiner

SUPPORTING DEVICE FOR DISPLAY DEVICE

CROSS-REFERENCE TO RELATED APPLICATION(S)

This application is based on and claims priority under 35 U.S.C. § 119 to Korean Patent Application No. 10-2018-0002427, filed on Jan. 8, 2018 in the Korean Intellectual Property Office, the disclosure of which is incorporated by reference herein in its entirety.

BACKGROUND

1. Technical Field

The present disclosure relates to a supporting device for supporting a display device on which an image is displayed.

2. Description of the Related Art

An ultrasonic imaging apparatus is an apparatus that irradiates an ultrasonic signal from a body surface of a target toward a target site in the body and obtains an image of a monolayer or blood flow of soft tissue without invasion by using information of a reflected ultrasonic signal (ultrasonic echo signal).

An image obtained by the ultrasonic imaging apparatus is displayed to a user by a display device. The display device may be coupled to a main body of the ultrasonic imaging apparatus by a supporting device including a multi-joint arm for the convenience of the user, Through the multi-joint arm, the user may freely move the position of the display device and confirm the image displayed on the display device.

The ultrasonic imaging apparatus described above is merely an example, and the display device as well as the ultrasonic imaging apparatus may be coupled to other apparatuses by a supporting device including a mufti-joint arm.

SUMMARY

It is an aspect of the present disclosure to provide a supporting device for a display device including a multi-joint arm, which can compensate for tilting of the display device caused by the multi-joint arm.

Additional aspects of the present disclosure will be set forth in part in the description which follows and, in part, will be obvious from the description, or may be learned by practice of the disclosure.

In accordance with an aspect of the present disclosure, a supporting device for a display device displaying an image includes a multi-joint arm including at least one joint, a hinge connected to one end of the multi-joint arm and rotatably coupled with the display device about a rotation axis extending in the front-rear direction of the display device, a damper to restrict rotation of the hinge to a certain extent to shorten a rotation time of the hinge when the hinge is rotated, and a brake to fix the hinge when the rotation of the hinge is finished, wherein the hinge is disposed on the same plane as the center of gravity of the display device in a vertical direction of the display device.

The hinge is disposed above the center of gravity of the display device in the vertical direction of the display device.

The damper includes a rotary type damper.

The supporting device further includes a controller to control the brake such that the brake brakes the hinge or the braking of the brake to the hinge is released.

The supporting device further includes a sensor to sense an external force when the external force is applied to the display device, wherein the controller is configured to release the braking of the brake when the external force is sensed by the sensor.

The sensor includes a touch sensor.

The sensor includes a switch sensor.

The controller controls the brake so that the brake stops the rotation of the hinge when the rotation of the hinge is completed by the damper.

The supporting device further includes a lever provided such that the brake brakes the hinge or the braking of the brake to the hinge is released.

The hinge includes a bracket coupled to the display device at a rear surface of the display device, a hinge shaft extending rearward of the bracket, and a hinge arm coupled to the hinge shaft to rotate the hinge shaft and connected to one end of the multi-joint arm.

The damper is provided to be coupled to one end of the hinge arm and to insert the hinge shaft.

The brake is provided to be coupled to the other end of the hinge arm and to restrain the hinge shaft to brake the hinge.

The brake is provided to brake the hinge when the display device is rotated by the hinge and then horizontally aligned with respect to the left and right direction of the display device.

The supporting device further includes a sensor to sense that the display device is horizontally aligned with respect to the left and right direction of the display device, wherein the controller is configured to brake the hinge when a horizontal value is sensed by the sensor.

The hinge is provided such that the rotation of the hinge is stopped by the weight of the display device.

In accordance with another aspect of the present disclosure, a supporting device for a display device displaying an image includes a multi-joint arm including at least one joint, and a hinge connected to one end of the mufti-joint arm and rotatably coupled with the display device about a rotation axis extending in the front-rear direction of the display device, wherein the hinge is provided on the same plane as the center of gravity of the display device in a vertical direction of the display device so that the rotation of the hinge is stopped by the weight of the display device, and disposed above the center of the display device in the vertical direction of the display device.

The supporting device further includes a damper to restrict rotation of the hinge to a certain extent to shorten a rotation time of the hinge when the hinge is rotated.

The supporting device further includes a brake to fix the hinge when the rotation of the hinge is finished.

The brake is provided to release the braking of the hinge when an external force is applied to the display device and to brake the hinge when the display device is rotated by the hinge and then horizontally aligned with respect to the left and right direction of the display device.

In accordance with another aspect of the present disclosure, an ultrasonic imaging apparatus includes a display device to display an image, and a supporting device to support the display device, wherein the supporting device includes a multi-joint arm including at least one joint, a hinge connected to one end of the multi-joint arm and rotatably coupled with the display device about a rotation axis extending in the front-rear direction of the display device, and disposed on the same plane as the center of gravity of the display device in a vertical direction of the display device, a damper to restrict rotation of the hinge to a certain extent to shorten a rotation time of the hinge when the hinge is rotated, and a brake to fix the hinge when the rotation of the hinge is finished.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
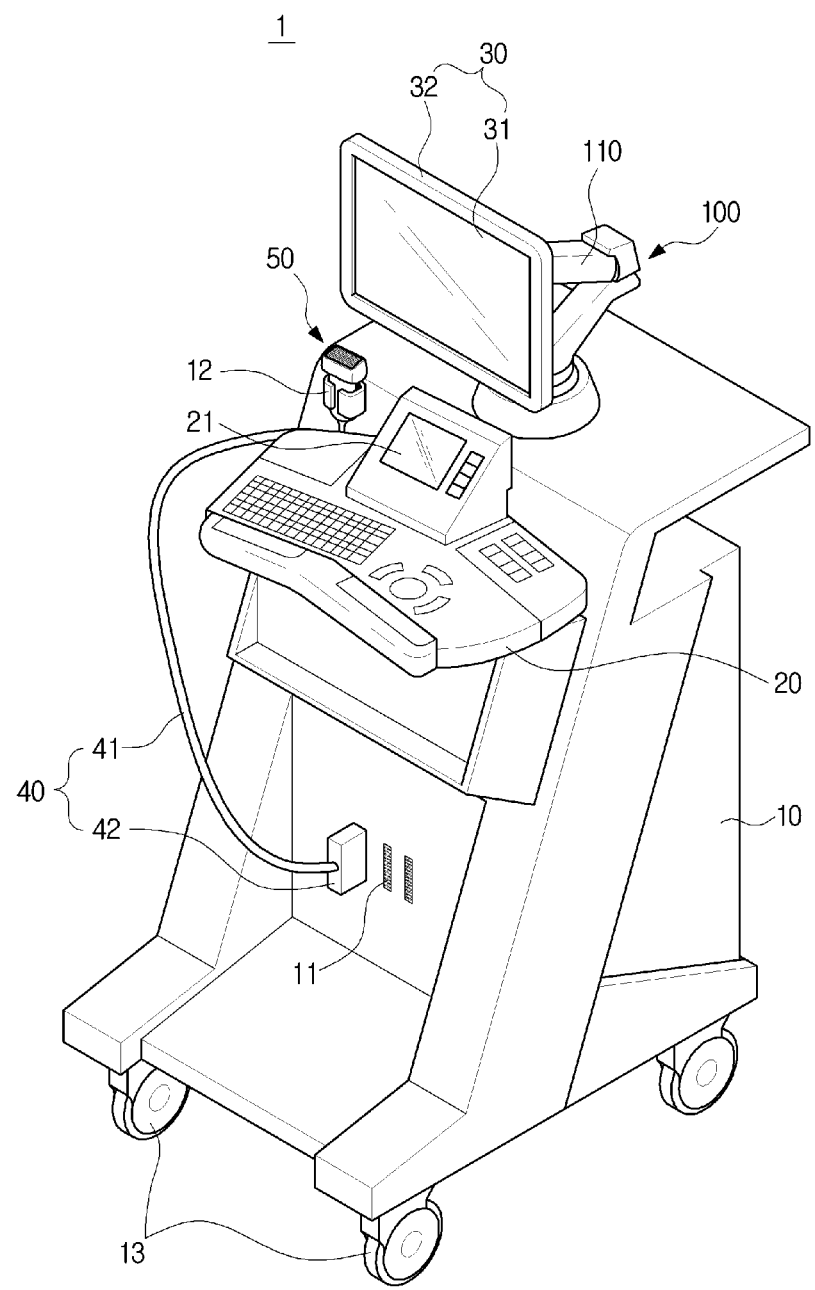
FIG. 1 is a view illustrating an ultrasonic imaging apparatus according to a first embodiment of the present disclosure.

The embodiments described herein and the configurations shown in the drawings are only examples of preferred embodiments of the present disclosure; and various modifications may be made at the time of filing of the present disclosure to replace the embodiments and drawings of the present application.

Like reference numbers or designations in the various drawings of the present application represent parts or components that perform substantially the same functions.

The terms used in this specification are for the purpose of describing the embodiments and are not intended to restrict and/or to limit the disclosure. The singular expressions may include plural expressions, unless the context clearly dictates otherwise. In this specification, the terms "comprises" and "has" are intended to indicate that there are features, numbers, steps, operations, elements, parts, or combinations thereof described in the specification, and do not exclude the presence or addition of one or more other features, numbers, steps, operations, elements, parts; or combinations thereof.

It will be understood that, although the terms first, second, etc. may be used herein to describe various components, these components should not be limited by these terms. These terms are only used to distinguish one component from another. For example, without departing from the scope of the present disclosure, the first component may be referred to as a second component, and similarly, the second component may also be referred to as a first component. The term "and/or" includes any combination of a plurality of related items or any one of a plurality of related items.

In this specification, the terms "front," "rear," "upper," "lower," "left," and "right" are defined with reference to the drawings, and the shape and position of each component are not limited by these terms.

A supporting device for a display device according to embodiments of the present disclosure will be described with respect to the supporting device for the display device coupled to an ultrasonic imaging apparatus, but is not limited thereto. For example, the supporting device for the display device according to embodiments of the present invention may be combined with an ultrasonic imaging apparatus, as well as another apparatus including a display device and a multi-joint arm supporting the display device.

Hereinafter, a first embodiment according to the present disclosure will be described in detail with reference to the accompanying drawings.

Figure 2:
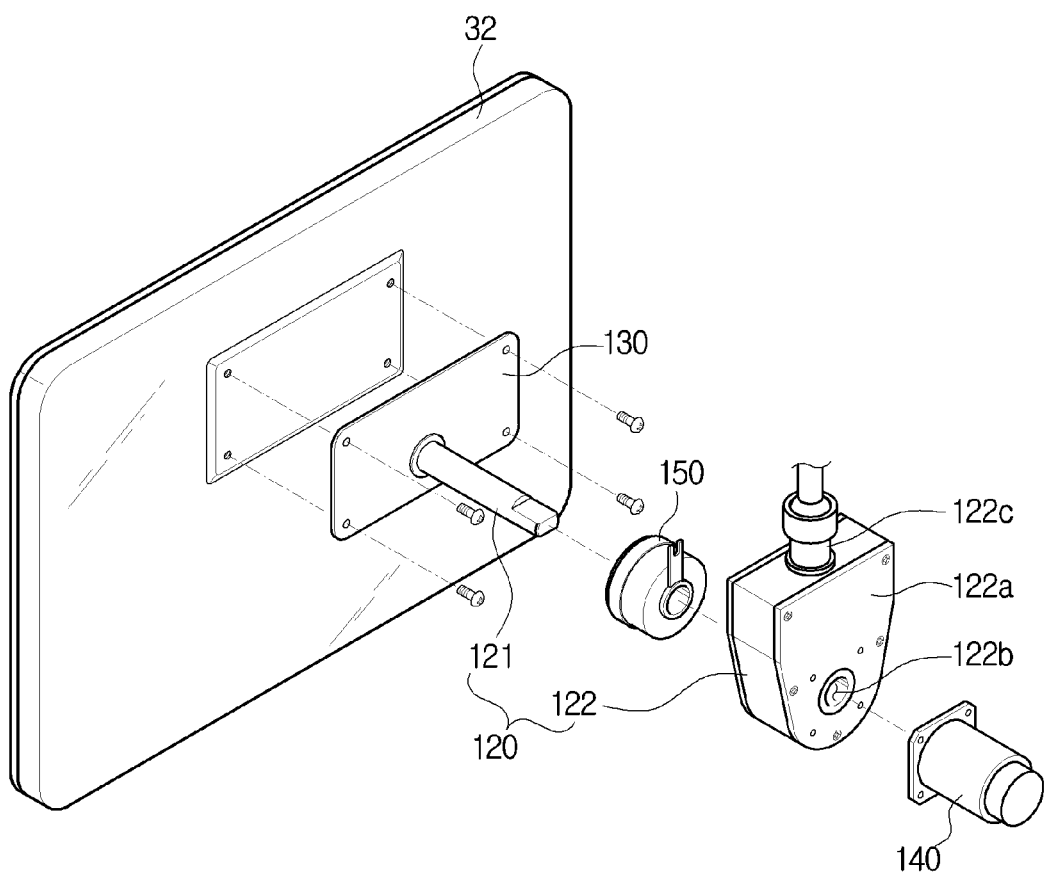
FIG. 2 is an exploded perspective view of a display device and a part of a supporting device for the display device according to the first embodiment of the present disclosure.
Figure 3A:
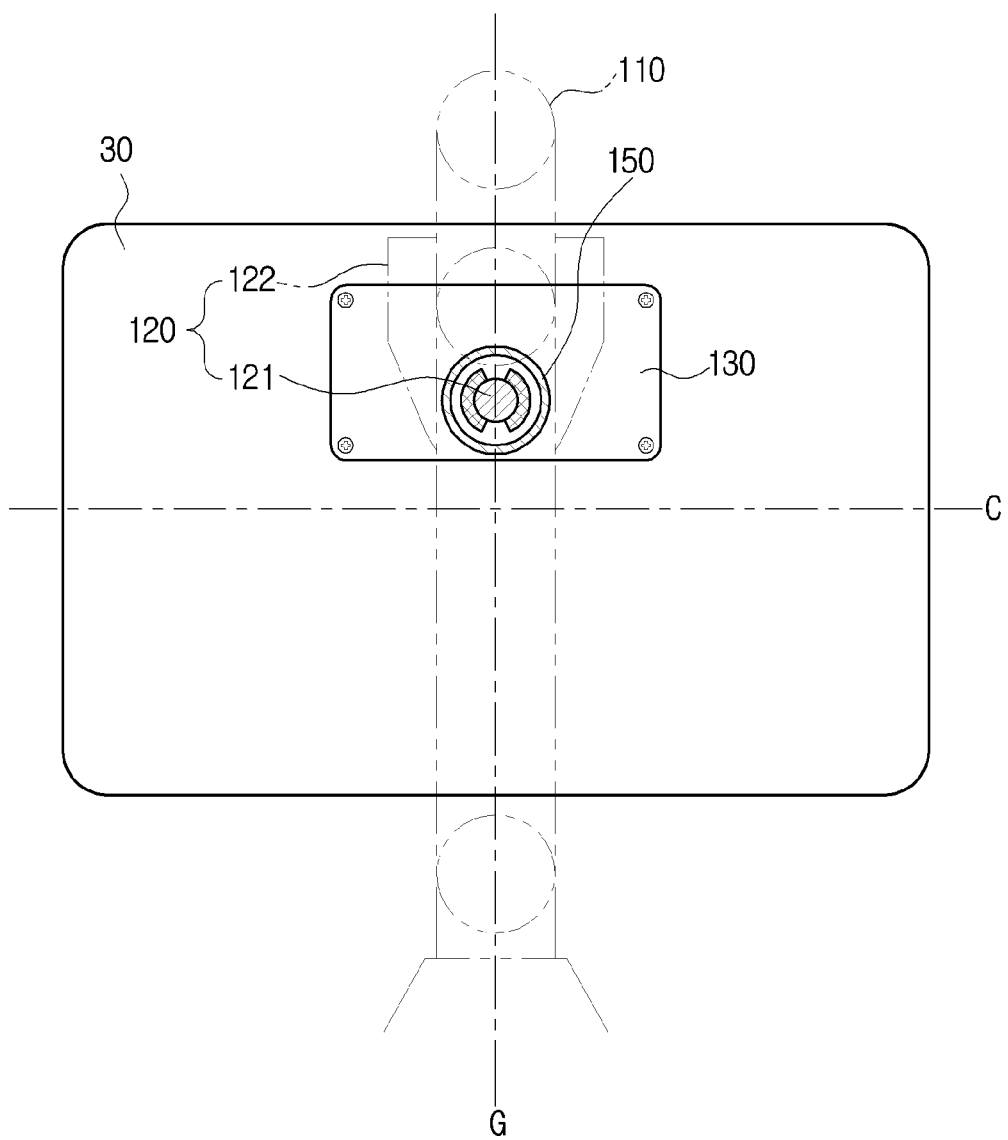
FIG. 3a is a front view schematically illustrating the display device and the supporting device for the display device according to the first embodiment of the present disclosure.
Figure 3B:
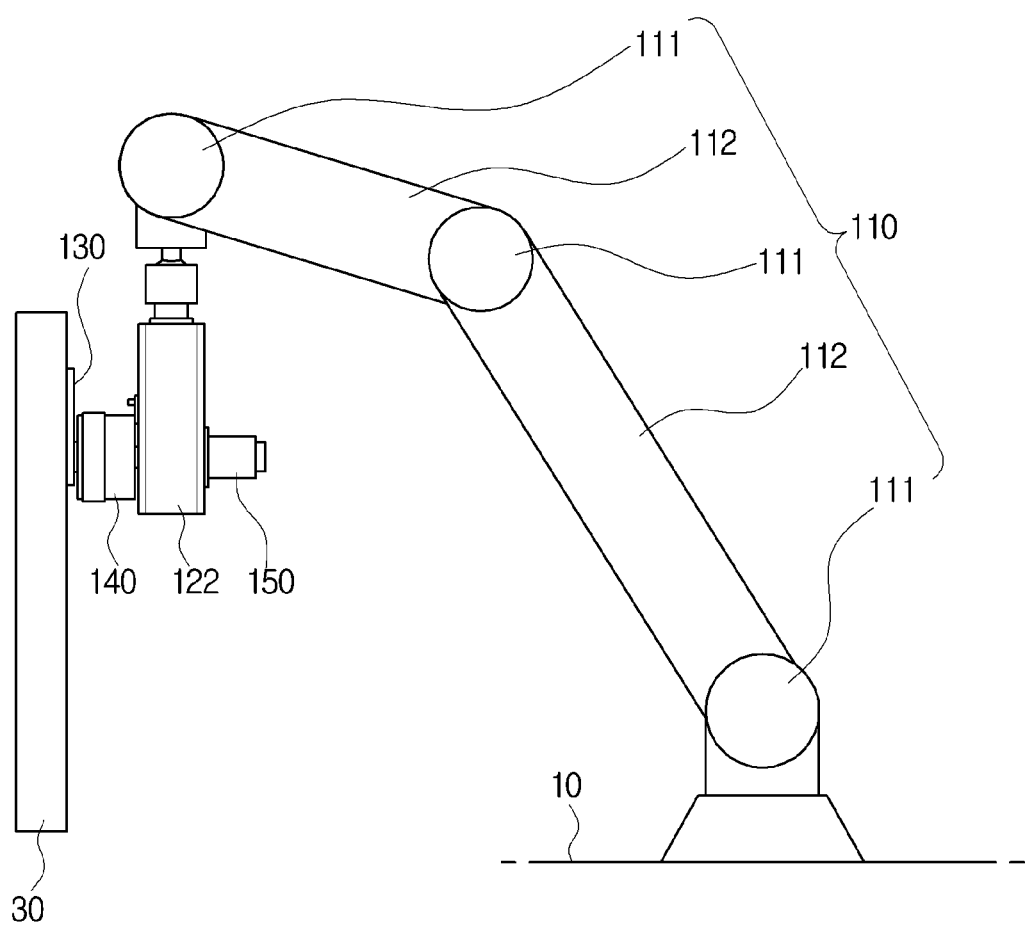
FIG. 3b is a side view schematically illustrating the display device and the supporting device for the display device according to the first embodiment of the present disclosure.

FIG. 1 is a view illustrating an ultrasonic imaging apparatus according to a first embodiment of the present disclosure, FIG. 2 is an exploded perspective view of a display device and a part of a supporting device for the display device according to the first embodiment of the present disclosure, FIG. 3a is a front view schematically illustrating the display device and the supporting device for the display device according to the first embodiment of the present disclosure, and FIG. 3b is a side view schematically illustrating the display device and the supporting device for the display device according to the first embodiment of the present disclosure.

Referring to FIG. 1, an ultrasonic imaging apparatus 1 according to a first embodiment of the present disclosure may include a main body 10, an input device 20, a display device 30, and an ultrasonic probe 50.

At least one connection portion 11 may be provided on one side of the main body 10. A connector 42 connected to a cable 41 may be physically coupled to the connection portion 11.

The main body 10 may include a holder 12 in which the ultrasonic probe 50 is put into. When a user does not use the ultrasonic imaging apparatus 1, the ultrasonic probe 50 may be put into and stored in the holder 12.

The main body 10 may include a moving device 13 provided at a lower side of the main body 10 to move the ultrasonic imaging apparatus 1. The moving device 13 may be a plurality of castors provided on the bottom surface of the main body 10. The castors may be aligned so as to allow the main body 10 to run in a specific direction or may be freely movable so that the ultrasonic imaging apparatus 1 may move in any direction. The moving device 13 may include a locking device (not shown) to stop at a specific location.

The ultrasonic probe 50 may contact the surface of a target object to transmit and receive ultrasonic signals. Specifically, the ultrasonic probe 50 may transmit an ultrasonic signal to a specific site in the target object according to a transmission signal transmitted from the main body 10 and receive an echo ultrasonic signal reflected from the specific site of the target object to transmit the echo ultrasonic signal to the main body. Herein, the echo ultrasonic signal may be an ultrasonic signal, which is an RF (Radio Frequency) signal reflected from the target object, but it is not limited thereto. For example, the echo ultrasonic signal may include all the signals produced by the reflection of the ultrasonic signal transmitted to the target object.

The target object may be a living body of a human being or an animal, but is not limited thereto. Any object may be used as long as its internal structure may be imaged by an ultrasonic signal.

The ultrasonic probe 50 may be connected to the main body 10 by a connecting member 40. The connecting member 40 may include the cable 41 and the connector 42. One side of the cable 41 may be connected to the ultrasonic probe 50 and the other side of the cable 41 may be connected to the connector 42. The connector 42 may be detachably mounted to the connection portion 11 provided in the main body 10. Accordingly, the ultrasonic probe 50 may be connected to the main body 10.

The ultrasonic probe 50 may be connected to the main body 10 by the connecting member 40 to receive various signals required for controlling the ultrasonic probe 50 through a wired communication network or to transmit an analog signal or a digital signal corresponding to the echo ultrasonic signal received by the ultrasonic probe 50.

Specifically, the wired communication network refers to a communication network capable of transmitting and receiving signals through a wired network. According to an embodiment, the main body 10 may transmit and receive various signals to and from the ultrasonic probe 50 using a wired communication network such as a PCI (Peripheral Component Interconnect), a PCI-express, and a USB (Universal Serial Bus), but is not limited thereto.

However, the ultrasonic probe 50 is not limited to the above, and may be connected to the main body 10 through a wireless communication network to receive various signals required for controlling the ultrasonic probe 50 or to transmit an analog signal or a digital signal corresponding to the echo ultrasonic signal received by the ultrasonic probe 50.

The main body 10 may be provided with the input device 20. The input device 20 may be provided in the form of a keyboard, a foot switch, or a foot pedal. When the input device 20 is a keyboard, the keyboard may be provided at an upper portion of the main body 10. The keyboard may include at least one of a switch, a key, a joystick, and a trackball. When the input device 20 is a foot switch or a foot pedal, the foot switch or the foot pedal may be provided at a lower side of the main body 10.

In addition, the input device 20 may be implemented in a software manner, such as a graphical user interface. In this case, the input device 20 may be displayed through a display 21.

The user may control the operation of the ultrasonic imaging apparatus 1 through the input device 20. For example, the input device 20 may receive a mode selection command such as A mode, B mode, M mode, or Doppler image. The input device 20 may also receive an ultrasonic diagnostic start command. The command input through the input device 20 may be transmitted to the main body 10 through wired communication or wireless communication.

The display device 30 may display the ultrasonic image obtained in the ultrasonic diagnostic process. The display device 30 may display an application related to the operation of the ultrasonic imaging apparatus 1.

The display device 30 may include a cathode ray tube (CRT) display panel, a liquid crystal display (LCD) panel, a light emitting diode (LED) panel, an organic light emitting diode (OLED) panel, a plasma display panel (PDP), and a field emission display (FED) panel, but it is not limited thereto.

The display device 30 may include a display 31 on which an image is displayed and a cover 32 of the display device 30. The cover 32 generally refers to a configuration of forming an appearance of the bezel or an exterior of the display 31 such as a housing of the display device 30.

The display device 30 may be provided to be coupled to the main body 10. The display device 30 may be coupled to the main body 10 by a supporting device 100 for a display device that is coupled to the main body 10.

The supporting device 100 for a display device may include a multi-joint arm 110 that may be rotated or moved in various directions. Accordingly, the user may press the display device 30 or the supporting device 100 for a display device to move the display device 30 to a position required by the user and arrange the display device 30 so that an image is displayed in a direction required by the user.

That is, the supporting device 100 for a display device having the multi-joint arm 110 including at least one joint may be disposed on an upper side of the main body 10 so that the user may be inspected in various postures and positions.

Specifically, one end of the supporting device 100 for a display device may be coupled to the display device 30 and the other end of the supporting device 100 for a display device may be coupled to an upper side of the main body 10. Also, the display device 30 may be disposed at various positions and in various directions by the multi-joint arm 110.

In the case of the supporting device for a display device, each component may be finely deformed due to the weight of a component such as the display device or the multi-joint arm, or a tolerance may occur in a connecting member such as a link connecting at least one joint, and thus the display device may be tilted.

In particular, the tilting phenomenon of the display device in the left-right direction does not cause any problems with respect to usability and safety of the display device or the supporting device for the display device, but may cause a user to feel uncomfortable when using the display device and may cause a problem that the feeling of use is deteriorated in terms of emotional aspects.

Accordingly, in the conventional case, by reinforcing the rigidity of the component having the largest deformation due to its own weight or the part of one component through the structural analysis of the multi-joint arm of the supporting device for a display device, the display device is prevented from tilting in the left and right direction by the deformation of the supporting device for the display device.

However, in such a case, there arise problems of an increase in the manufacturing cost due to a change of the processing method, an increase in the manufacturing cost due to a change in the material or the reinforcement of the material, and a weight increase because rigidity is reinforced by changing the material and processing method of some components.

Further, in the conventional case, by predicting the tilting of the display device and accordingly applying a correction angle to the hinges or links connecting the joints of the supporting device for the display device in advance, the tilting of the display device in the left and right direction is prevented, That is, the joint portion may be corrected so that the tilting of the display device at the most tilted position is minimized.

However, in the case of such correction, different correction angles are required depending on the type of multi-joint arm, and due to the nature of the degree of freedom of the multi-joint arm, the correction angle at every position of the display device may not be corrected to the joint of the multi-joint arm. Accordingly, the tilting of the display device may be compensated at some positions of the display device, but the tilting of the display device may not be compensated at any position. In addition, since it is necessary to apply different correction angles according to the material of the multi-joint arm, the number of joints, and the like, there may be a problem with the manufacturing cost in production.

In order to prevent the above problems from occurring, the supporting device 100 for a display device according to the present disclosure, despite the use of the conventionally used multi-joint arms, may be provided to compensate for tilting even at all positions of the display device 30 without applying additional material to the multi-joint arm 110 and reinforcement according to the change of the manufacturing method or correction angle according to the structure design in advance.

Specifically, the supporting device 100 for a display device according to the present disclosure may include a hinge 120 for coupling the multi-joint arm 110 and the display device 30, That is, one end of the multi-joint arm 110 may be coupled to the hinge 120, the other end of the multi-joint arm 110 may be coupled to the main body 10, one end of the hinge 120 may be coupled to a rear surface of the display device 30, and the other end of the hinge 120 may be coupled to the one end of the multi-joint arm 110.

The hinge 120 may include a hinge shaft 121 coupled to the display device 30, and a hinge arm 122 into which the hinge shaft 121 is inserted and to which the hinge shaft 121 is rotatably coupled.

The hinge shaft 121 may be coupled to a bracket 130 coupled to the rear surface of the display device 30 and disposed at the rear surface of the display device 30. However, the hinge shaft 121 may be integrally formed with the bracket 130 as shown in FIG. 2, and the hinge shaft 121 and the bracket 130 may be coupled to each other as a separate structure.

The hinge shaft 121 may protrude rearward of the display device 30 and extend in the front-rear direction with respect to the display 31 of the display device 30.

The hinge arm 122 may include an insertion groove 122b into which a hinge body 122a and the hinge shaft 121 are inserted and a coupling portion 122c coupled to one end of the multi-joint arm 110.

The coupling portion 122c may be coupled to one end of the multi-joint arm 110 through a ball joint as shown in FIGS. 2 and 3b, but is not limited thereto. For example, the coupling portion 122c may be coupled through various types of joints or may be directly coupled to the multi-joint arm 110 without joints.

The supporting device 100 for a display device may also include a damper 140 provided to restrict the rotation of the hinge shaft 121 so as to shorten the rotation time of the display device 30 when the display device 30 is rotated by the hinge shaft 121.

The damper 140 may be coupled to one side of the hinge body 122a, The hinge shaft 121 may be inserted into the damper 140, and the damper 140 may reduce the number of times the display device 30 rotates about the hinge shaft 121 by restricting the rotation of the hinge shaft 121 inserted into the damper 140.

The damper 140 may include a rotary type damper. Accordingly, the damper 140 may reduce the rotation of the hinge shaft 121 that is rotated inside the damper 140. However, the damper 140 is not limited thereto, and may include other configurations that may restrict the rotation of the hinge shaft 121 besides the rotary type damper.

The supporting device 100 for a display device may further include a brake 150 for braking the hinge shaft 121 to fix the hinge 120.

The hinge shaft 121 may be inserted into the brake 150, the insertion groove 122b, and the damper 140 sequentially. However, the present disclosure is not limited thereto, and the order and position in which the hinge shaft 121 is inserted may be variously changed.

The brake 150 may brake the hinge shaft 121 inserted into the brake 150 in a mechanical friction method or an electromagnetic method. That is, the various braking method may be various applied to the brake 150.

The brake 150 may be coupled to the other side of the hinge body 122a, but is not limited thereto. For example, the brake 150 may be coupled to one side of the hinge body 122a and disposed in the same direction as the damper 140 with respect to the hinge body 122a, or the damper 140 and the brake 150 may be coupled to the hinge body 122a on the opposite side.

As shown in FIGS. 3a and 3b, the hinge 120 may be disposed on the same plane as a center of gravity G of the display device 30 in a vertical direction of the display device 30. Also, the hinge 120 may be disposed above a center C of the display device 30 in the vertical direction of the display device 30.

Specifically, the hinge shaft 121 may be disposed on the same plane as the center of gravity G of the display device 30 and disposed above the center C of the display device 30, in the vertical direction of the display device 30.

The display device 30 may be rotated with respect to the hinge arm 122 with the hinge shaft 121 as a rotation axis. That is, the display device 30 may be coupled to rotate about one end of the multi-joint arm 110.

Since the hinge shaft 121, which is a rotation axis of the display device 30, is disposed on the center of gravity of the display device 30, the display device 30 may be rotated about the hinge shaft 121 by the weight of the display device 30 when the display device 30 is disposed to be tilted to a certain extent in the left and right direction.

The rotation of the display device 30 may be finished when the left and right sides of the display device 30 become parallel after the display device 30 is rotated until the left and right sides of the display device 30 are balanced by the weight of the display device 30. This will be described in detail below.

Figure 4A:
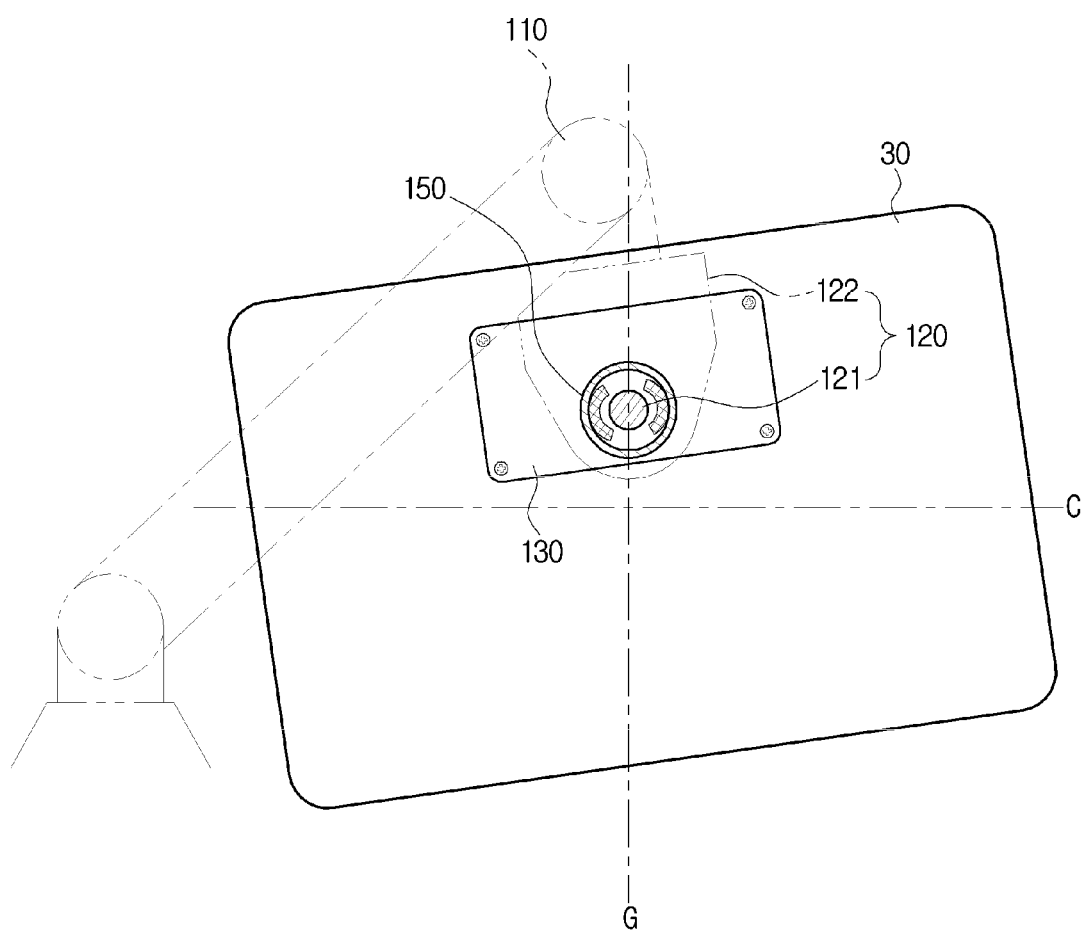
FIG. 4a is a front view schematically illustrating a state in which the display device and the supporting device for the display device according to the first embodiment of the present disclosure are tilted.
Figure 4B:
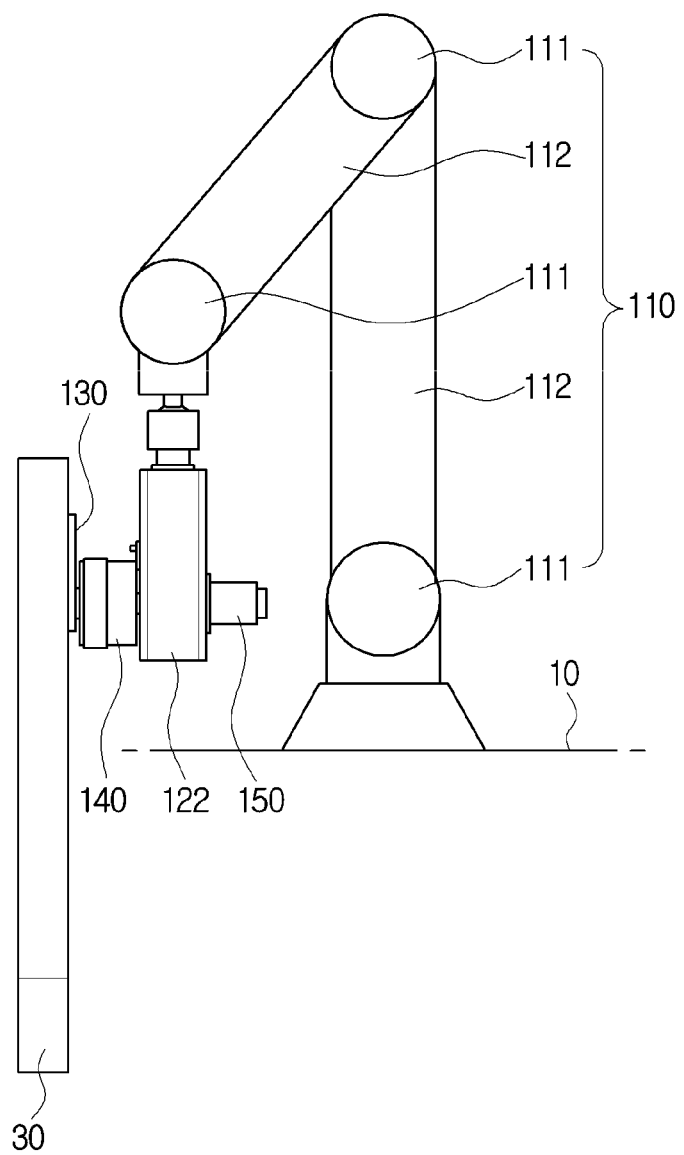
FIG. 4b is a side view schematically illustrating a state in which the display device and the supporting device for the display device according to the first embodiment of the present disclosure are tilted.
Figure 5A:
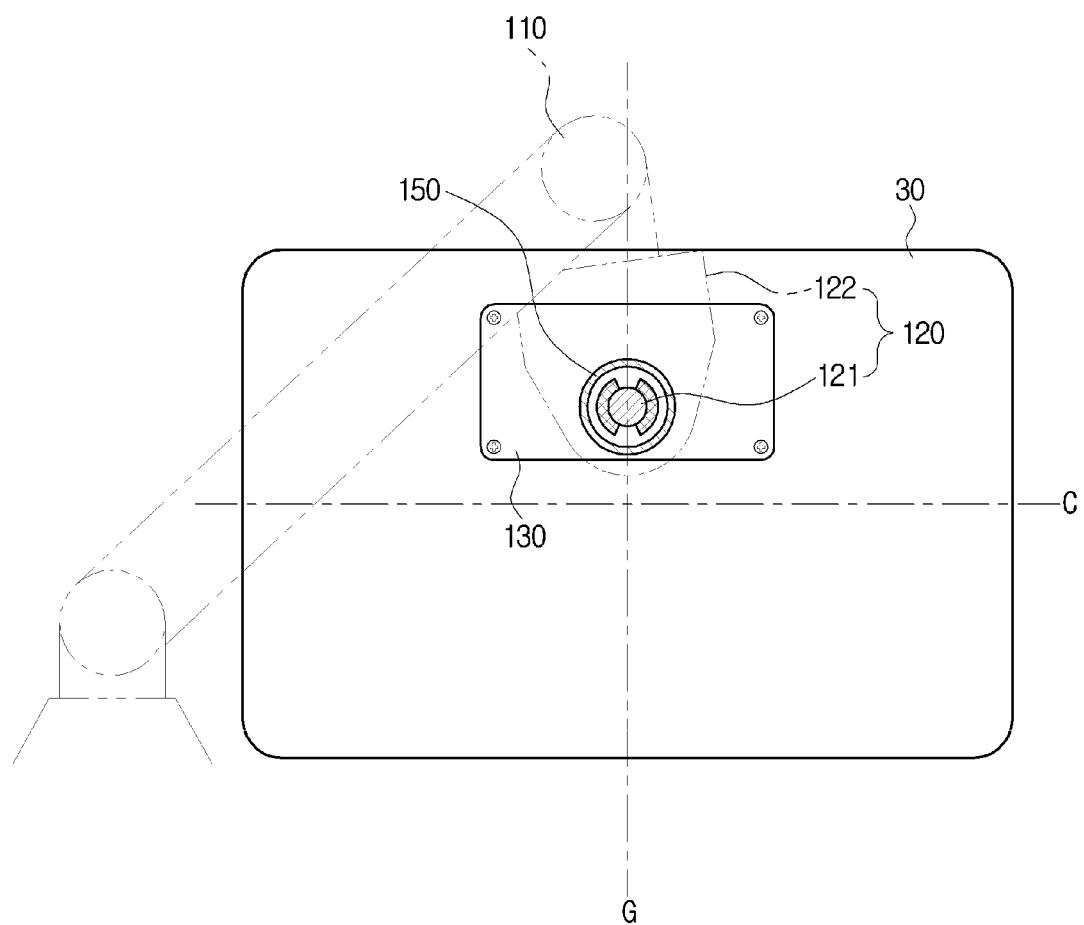
FIG. 5a is a front view schematically illustrating a state in which the display device and the supporting device for the display device according to the first embodiment of the present disclosure are compensated for tilting.
Figure 5B:
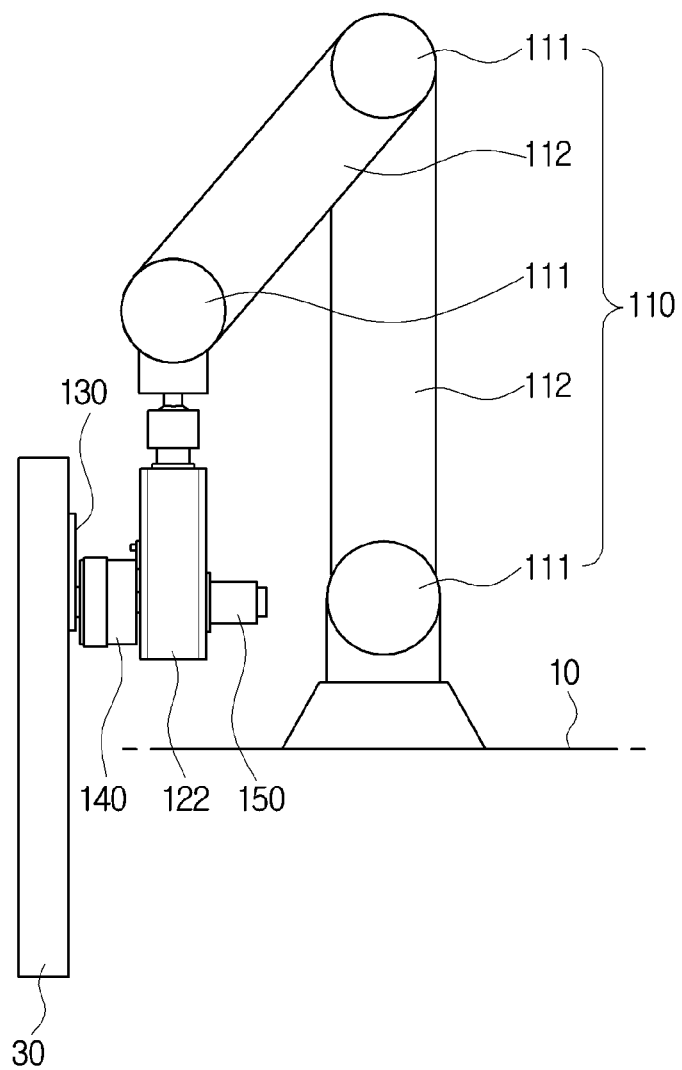
FIG. 5b is a side view schematically illustrating a state in which the display device and the supporting device for the display device according to the first embodiment of the present disclosure are compensated for tilting.
Figure 6:
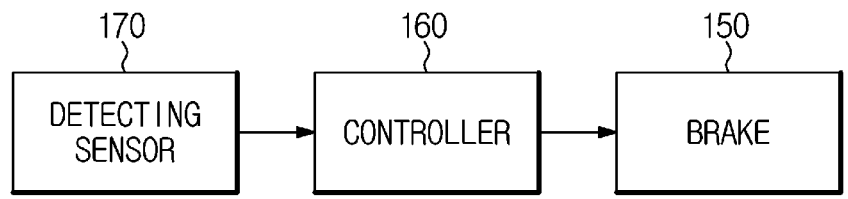
FIG. 6 is a schematic block diagram of a control of compensating for tilting of the supporting device for the display device according to the first embodiment of the present disclosure.

FIG. 4a is a front view schematically illustrating a state in which the display device and the supporting device for the display device according to the first embodiment of the present disclosure are tilted, FIG. 4b is a side view schematically illustrating a state in which the display device and the supporting device for the display device according to the first embodiment of the present disclosure are tilted, FIG. 5a is a front view schematically illustrating a state in which the display device and the supporting device for the display device according to the first embodiment of the present disclosure are compensated for tilting, FIG. 5b is a side view schematically illustrating a state in which the display device and the supporting device for the display device according to the first embodiment of the present disclosure are compensated for tilting, and FIG. 6 is a schematic block diagram of a control of compensating for tilting of the supporting device for the display device according to the first embodiment of the present disclosure.

As described above, the display device 30 may be disposed toward a position or direction required by the user for the convenience of the user. The display device 30 may be disposed in any position and direction in a state of being coupled with the main body 10 through the multi-joint arm 110.

As shown in FIGS. 4a and 4b, the user may press the display device 30 to place the display device 30 at a position required by the user, and the multi-joint arm 110 may be provided such that joints 111 are rotated or a plurality of links 112 connected to the joints 111 are moved to place the display device 30 at an arbitrary position.

At this time, as the shape of the multi-joint arm 110 is changed, the gravity direction of its own weight formed by the multi-joint arm 110 may be changed, and thus the left or right side of the display device 30 may be tilted.

When one side of the display device 30 is tilted, the display device 30 may be rotated with the hinge shaft 121 as a rotation axis as described above. The display device 30 may be rotated until the left and right sides are horizontal, and as shown in FIGS. 5a and 5b, when the left and right sides are horizontal, the gravity of the left and right sides are balanced, so that the rotation of the display device 30 may be stopped by its own weight.

That is, even if the user arbitrarily moves the display device 30, the tilting of the display device 30 caused thereby may be compensated through the rotation of the display device 30 caused by the hinge 120.

Accordingly, since the display device 30 itself may be rotated through the hinge 120 so that the left and right sides of the display device 30 are horizontal even if the rigidity of some components of the multi-joint arm 110 is not reinforced or the correction angle is not applied to the joints of the multi-joint arm 110 in advance as in the conventional art, the tilting of the display device 30 may be simply corrected.

The tilting of the display device 30 that may occur as the display device 30 is disposed at an arbitrary position may be corrected by the rotation of the display device 30 caused by the hinge 120. That is, even if the supporting device 100 for a display device does not include a separate structure for compensating for the tilting of the display device 30, the supporting device 100 for a display device may correct the tilting of the display device 30 simply by rotating the display device 30 by its own weight.

As described above, the display device 30 is hinged to the multi-joint arm 110. When the display device 30 is pressed, the display device 30 may perform the pendulum motion with the hinge 120 as a rotation axis.

When the pendulum motion time of the display device 30 becomes longer, the user may feel fatigue while watching the display device 30. In order to prevent such a case, the supporting device 100 for a display device may include the damper 140.

The damper 140 may include a rotary type damper as described above. The damper 140 may restrict the rotational motion of the hinge shaft 121 by reducing the force of rotation of the hinge shaft 121 inserted in the damper 140 in the clockwise and counterclockwise directions.

Accordingly, the pendulum motion time of the display device 30 that uses the hinge shaft 121 as a rotation axis may be reduced, and the usability of the display device 30 may be improved by rapidly moving the display device 30 horizontally in the left and right direction.

The pendulum motion time and the amplitude of the pendulum motion may be determined according to the weight of the display device 30 and the arrangement of the hinge shaft 121, and the damper 140 may be designed to minimize the pendulum motion time of the display device 30 in consideration of the weight of the display device 30 and the position of the hinge shaft 121.

Also, as described above, the display device 30 is hinged to the multi-joint arm 110, and thus the display device 30 may be rotated by the hinge 120 even if the display device 30 is very weakly pressed. In order to prevent such a case, the supporting device 100 for a display device includes the brake 150.

The brake 150 may brake the hinge shaft 121 to prevent the hinge 120 from rotating and thereby prevent the display device 30 from rotating.

The brake 150 may be provided to release the braking of the hinge shaft 121 when the user moves the display device 30 so that the tilting of the display device 30 due to the rotation after the movement may be corrected.

Further, when the correction of the tilting of the display device 30 is completed, the brake 150 again may prevent the display device 30 from rotating by braking the hinge shaft 121.

As shown in FIG. 6, the supporting device 100 for a display device may include a controller 160 for controlling the brake 150. The supporting device 100 for a display device may also include a detecting sensor 170 for sensing an external force transmitted to the display device 30.

The detecting sensor 170 may transmit an electrical signal to the controller 160 when sensing an external force. The detecting sensor 170 may include a touch sensor that senses the user's touch.

The touch sensor may be disposed on the cover 32 of the display device 30 and transmit an electrical signal generated by the user's touch when the user presses the cover 32 to move the display device 30 to the controller 160.

The touch sensor is not limited thereto and may be disposed on the display 31 as well as the cover 32 so that the touch sensor may transmit information on the touch of the user to the controller 160 regardless of where the user touches the display device 30.

The controller 160 that has received the signal from the detecting sensor 170 may control the brake 150 to release the braking of the brake 150. Accordingly, when the user presses the cover 32, the braking of the brake 150 may be released by the controller 160 and the position of the display device 30 may be changed by the user, and as a result, the shape of the multi-joint arm 110 may be changed.

The tilting of the display device 30 may occur after the shape of the multi-joint arm 110 is changed but the tilting may be corrected by the rotation of the display device 30 about the hinge shaft 121.

After the user places the display device 30 at a desired position, the pressing of the display device 30 is finished. At this time, the touch sensor of the detecting sensor 170 senses that the touch of the user is interrupted and may transmit the information to the controller 160 again.

The controller 160 may control the brake 150 so that the brake 150 brakes the hinge 120 after a predetermined time has elapsed since the reception of the information. That is, after the user finishes pressing the display device 30, the tilting of the display device 30 may occur, and thus the display device 30 may be rotated about the hinge shaft 121. The controller 160 may be configured such that the brake 150 may brake the hinge shaft 121 after a predetermined time has elapsed.

The predetermined time may be set in the controller 160 based on the time when the rotation of the display device 30 is finished through the damper 140.

When the brake 150 brakes the hinge 120 again by the controller 160, the rotation of the display device 30 is restricted, and thus the display device 30 may be fixed to one end of the multi-joint arm 110 in a state where the left and right direction of the display device 30 is horizontal.

Accordingly, the hinge shaft 121 may be maintained in a state of being braked by the brake 150 until the user thereafter touches the cover 32 to further move the position of the display device 30.

Hereinafter, a second embodiment and a third embodiment according to the present disclosure will be described. The configurations other than the sensor, the controller, and the brake, which will be described below, are the same as those of the first embodiment according to the present disclosure, and therefore, duplicate description will be omitted.

Figure 7:
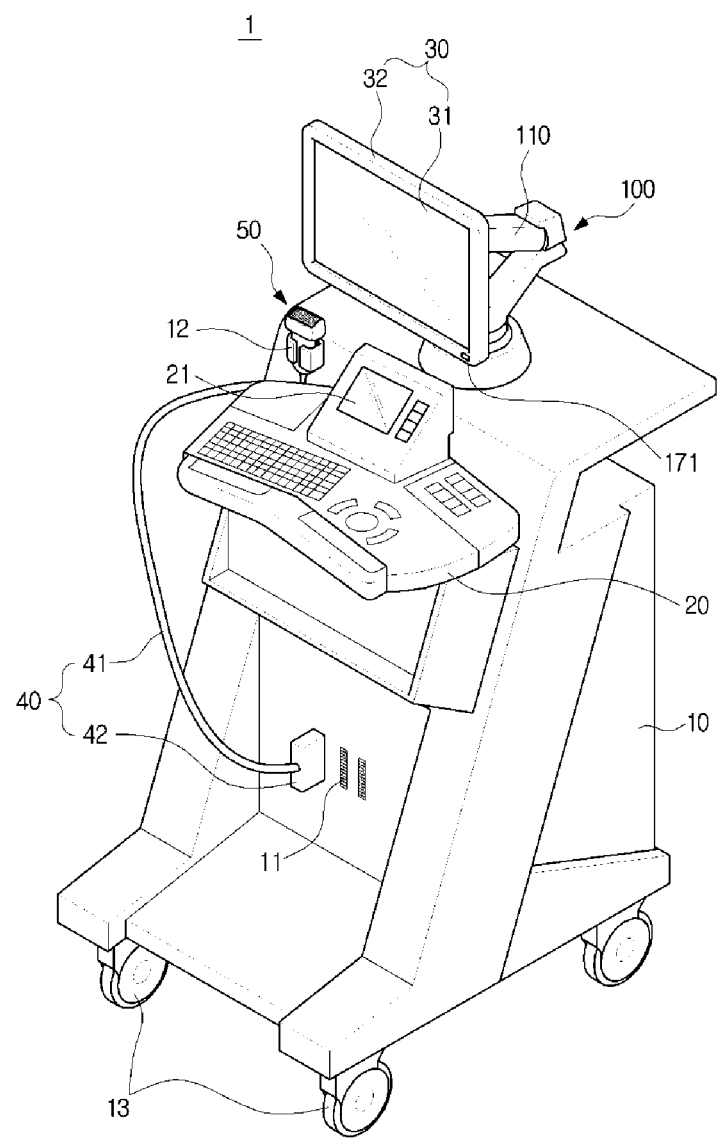
FIG. 7 is a view illustrating an ultrasonic imaging apparatus according to a second embodiment of the present disclosure.
Figure 8A:
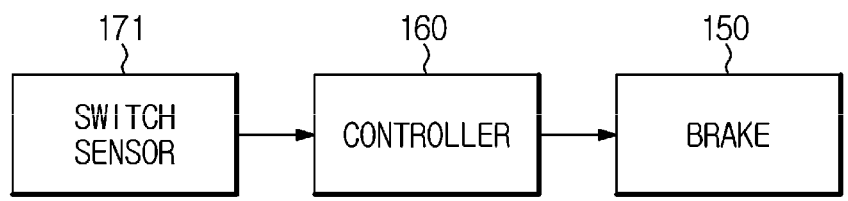
FIG. 8a is a schematic block diagram of a control of compensating for tilting of a supporting device for a display device according to the second embodiment of the present disclosure.
Figure 8B:
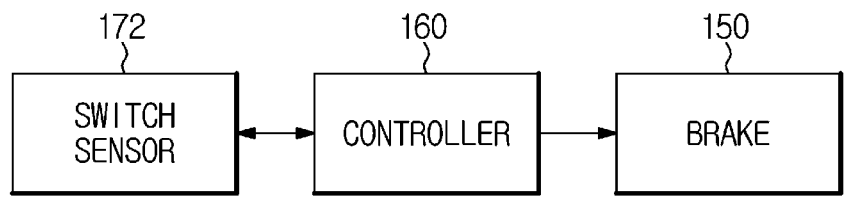
FIG. 8b is a schematic block diagram of a control of compensating for tilting of a supporting device for a display device according to a third embodiment of the present disclosure.

FIG. 7 is a view illustrating an ultrasonic imaging apparatus according to a second embodiment of the present disclosure, FIG. 8a is a schematic block diagram of a control of compensating for tilting of a supporting device for a display device according to the second embodiment of the present disclosure, and FIG. 8b is a schematic block diagram of a control of compensating for tilting of a supporting device for a display device according to a third embodiment of the present disclosure.

As shown in FIGS. 7 and 8a, the supporting device 100 for a display device according to the second embodiment of the present disclosure may include a switch sensor 171 that allows the user to rotate the display device 30 relative to the multi-joint arm 110 in order to move the display device 30.

The switch sensor 171 may be disposed on the cover 32 of the display device 30 so that the user may easily press the switch sensor 171. However, the present disclosure is not limited thereto, and the switch sensor 171 may be disposed in another configuration such as on the main body 10 or the like.

The switch sensor 171 may transmit information about the pressing of the switch sensor 171 to the controller 160 when the user presses the switch sensor 171. That is, the switch sensor 171 may be turned 'on' by the pressing of the switch sensor 171 by the user and transmit the value to the controller 160.

The controller 160 that has received the 'on' information from the switch sensor 171 may control the brake 150 to release the braking of the brake 150. Accordingly, when the user presses the switch sensor 171, the braking of the brake 150 may be released by the controller 160 and the position of the display device 30 may be changed by the user, and as a result, the shape of the multi-joint arm 110 may be changed.

The tilting of the display device 30 may occur after the shape of the multi-joint arm 110 is changed but the tilting may be corrected by the rotation of the display device 30 about the hinge shaft 121.

After the user places the display device 30 at a desired position, when the tilting of the display device 30 is finally corrected, the user may press the switch sensor 171 again to finish the movement of the display device 30.

At this time, the switch sensor 171 may transmit 'off' information by the pressing of the user to the controller 160 again.

The controller 160 may control the brake 150 so that the brake 150 brakes the hinge 120 after a predetermined time has elapsed since the reception of the 'off' information. That is, after the user finishes pressing the display device 30, the tilting of the display device 30 may occur, and thus the display device 30 may be rotated about the hinge shaft 121. The controller 160 may be configured such that the brake 150 may brake the hinge shaft 121 after a predetermined time has elapsed.

Alternatively, the controller 160 may control the brake 150 so that the brake 150 brakes the hinge 120 immediately after receiving the 'off' information. This is because the user may press the switch sensor 171 after the correction for the tilting of the display device 30 is finished. The control of the brake 150 by the controller 160 after a predetermined time has elapsed or the immediate control of the brake 150 by the controller 160 may be set arbitrarily according to the convenience of the user.

Although not shown in the drawings, the supporting device 100 for a display device may include a lever instead of the switch sensor 171. The lever may be disposed on the cover 32 or other configuration so that when the user presses the lever, the corresponding information may be received by the controller 160 to control the brake 150.

That is, not only an electric signal is transmitted to the controller 160 as in the touch sensor of the first embodiment or the switch sensor 171 of the second embodiment, but also a physical signal is transmitted through the lever, so that the controller 160 may control the brake 150.

The present disclosure is not limited thereto, and the lever may be directly engaged with the brake 150 to implement the braking and releasing of the brake 150 by directly pressing the lever without the controller 160.

As shown in FIG. 8b, the supporting device 100 for a display device according to the third embodiment of the present disclosure may include a switch sensor 172 that allows the user to rotate the display device 30 relative to the multi-joint arm 110 in order to move the display device 30.

The switch sensor 172 may be disposed on the cover 32 of the display device 30 so that the user may easily press the switch sensor 172, However, the present disclosure is not limited thereto, and the switch sensor 172 may be disposed in another configuration such as on the main body 10 or the like.

The switch sensor 172 may transmit information about the pressing of the switch sensor 172 to the controller 160 when the user presses the switch sensor 172. That is, the switch sensor 172 may be turned 'on' by the pressing of the switch sensor 172 by the user and transmit the value to the controller 160.

The controller 160 that has received the 'on' information from the switch sensor 172 may control the brake 150 to release the braking of the brake 150. Accordingly, when the user presses the switch sensor 172, the braking of the brake 150 may be released by the controller 160 and the position of the display device 30 may be changed by the user, and as a result, the shape of the multi-joint arm 110 may be changed.

The tilting of the display device 30 may occur after the shape of the multi-joint arm 110 is changed but the tilting may be corrected by the rotation of the display device 30 about the hinge shaft 121.

The controller 160 may control the brake 150 so that the brake 150 again brakes the hinge 120 after a predetermined time has elapsed since the reception of the information from the switch sensor 172.

That is, the user may start moving the display device 30 while pressing the switch sensor 172, and in order to solve the inconvenience that the user presses the switch sensor 172 again after the movement of the display device 30 is finished, the controller 160 may control the brake 150 so that the braking of the brake 150 is released when the user presses the switch sensor 172 and the brake 150 brakes the hinge 120 again after a predetermined time even though no information is received from the switch sensor 172.

The controller 160 may control the brake 150 to brake the hinge 120 and then control the switch sensor 172 such that the switch sensor 172 has the value of 'off' again from the 'on' value. Accordingly, even if the user presses the switch sensor 172 only once, the display device 30 may be easily moved and then the display device 30 may be fixed.

A predetermined time value at which the controller 160 starts to control the brake 150 again may be arbitrarily set by the user.

Hereinafter, a fourth embodiment according to the present disclosure will be described. The configurations other than the sensor, the controller, and the brake, which will be described below, are the same as those of the first embodiment according to the present disclosure, and therefore, duplicate description will be omitted.

Figure 9:
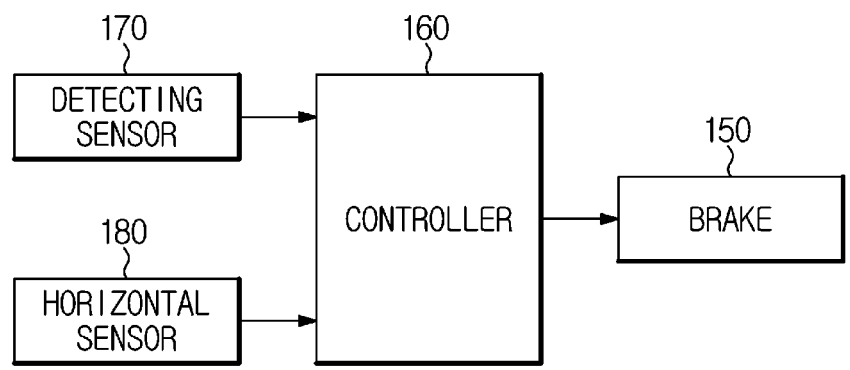
FIG. 9 is a schematic block diagram of a control of compensating for tilting of a supporting device for a display device according to a fourth embodiment of the present disclosure.

FIG. 9 is a schematic block diagram of a control of compensating for tilting of a supporting device for a display device according to a fourth embodiment of the present disclosure.

As shown in FIG. 9, the supporting device 100 for a display device according to a fourth embodiment of the present disclosure may further include a horizontal sensor 180 for sensing a horizontal position of the display device 30 in addition to the detecting sensor 170 for sensing an external force generated by a user.

The horizontal sensor 180 may transmit information on when the display device 30 is horizontally moved in the left and right direction after the rotation of the display device 30, to the controller 160.

That is, the controller 160 may release the braking of the brake 150 through the information received from the detecting sensor 170, and may control the brake 150 to brake the hinge 120 again through the information received from the horizontal sensor 180.

Accordingly, the controller 160 may control the brake 150 through information received from the detecting sensor 170 and the horizontal sensor 180, respectively.

As is apparent from the above, the supporting device for a display device according to the present disclosure includes a hinge disposed on the center of gravity of the display device so that the tilting of the display device can be easily compensated by the weight of the display device without compensation by an additional configuration.

The embodiments described in the present specification and the configurations shown in the drawings are only examples of preferred embodiments of the disclosure, and it will be understood that various modifications may be made thereto at the time of filing of the present application to replace the embodiments of the present specification and the drawings.

What is claimed is:

1. A supporting device for a display device displaying an image, comprising:
   a multi-joint arm including at least one joint;
   a hinge connected to one end of the multi-joint arm and rotatably coupled with the display device about a rotation axis extending in the front-rear direction of the display device;
   a damper to restrict rotation of the hinge to a certain extent to shorten a rotation time of the hinge when the hinge is rotated; and
   a brake to fix the hinge when the rotation of the hinge is finished,
   wherein the hinge is disposed on the same plane as the center of gravity of the display device in a vertical direction of the display device.

2. The supporting device according to claim 1,
   wherein the hinge is disposed above the center of gravity of the display device in the vertical direction of the display device.

3. The supporting device according to claim 1,
   wherein the damper includes a rotary type damper.

4. The supporting device according to claim 1, further comprising:
   a controller to control the brake such that the brake brakes the hinge or the braking of the brake to the hinge is released.

5. The supporting device according to claim 4, further comprising:
   a sensor to sense an external force when the external force is applied to the display device,
   wherein the controller is configured to release the braking of the brake when the external force is sensed by the sensor.

6. The supporting device according to claim 5,
   wherein the sensor includes a touch sensor.

7. The supporting device according to claim 5,
   wherein the sensor includes a switch sensor.

8. The supporting device according to claim 4,
   wherein the controller controls the brake so that the brake stops the rotation of the hinge when the rotation of the hinge is completed by the damper.

9. The supporting device according to claim 1, further comprising:
   a lever provided such that the brake brakes the hinge or the braking of the brake to the hinge is released.

10. The supporting device according to claim 1,
    wherein the hinge includes a bracket coupled to the display device at a rear surface of the display device, a hinge shaft extending rearward of the bracket, and a hinge arm coupled to the hinge shaft to rotate the hinge shaft and connected to one end of the multi-joint arm.

11. The supporting device according to claim 10,
    wherein the damper is provided to be coupled to one end of the hinge arm and to insert the hinge shaft.

12. The supporting device according to claim 11,
    wherein the brake is provided to be coupled to the other end of the hinge arm and to restrain the hinge shaft to brake the hinge.

13. The supporting device according to claim 1,
    wherein the brake is provided to brake the hinge when the display device is rotated by the hinge and then horizontally aligned with respect to the left and right direction of the display device.

14. The supporting device according to claim 4, further comprising:
   a sensor to sense that the display device is horizontally aligned with respect to the left and right direction of the display device,
   wherein the controller is configured to brake the hinge when a horizontal value is sensed by the sensor.

15. The supporting device according to claim 13, wherein the hinge is provided such that the rotation of the hinge is stopped by the weight of the display device.

16. A supporting device for a display device displaying an image, comprising:
   a multi-joint arm including at least one joint; and
   a hinge connected to one end of the multi-joint arm and rotatably coupled with the display device about a rotation axis extending in the front-rear direction of the display device,
   wherein the hinge is provided on the same plane as the center of gravity of the display device in a vertical direction of the display device so that the rotation of the hinge is stopped by the weight of the display device, and disposed above the center of the display device in the vertical direction of the display device.

17. The supporting device according to claim 16, further comprising:
   a damper to restrict rotation of the hinge to a certain extent to shorten a rotation time of the hinge when the hinge is rotated.

18. The supporting device according to claim 16, further comprising:
   a brake to fix the hinge when the rotation of the hinge is finished.

19. The supporting device according to claim 18,
   wherein the brake is provided to release the braking of the hinge when an external force is applied to the display device and to brake the hinge when the display device is rotated by the hinge and then horizontally aligned with respect to the left and right direction of the display device.

20. An ultrasonic imaging apparatus comprising:
   a display device to display an image; and
   a supporting device to support the display device,
   wherein the supporting device comprises:
   a multi-joint arm including at least one joint;
   a hinge connected to one end of the multi-joint arm and rotatably coupled with the display device about a rotation axis extending in the front-rear direction of the display device, and disposed on the same plane as the center of gravity of the display device in a vertical direction of the display device;
   a damper to restrict rotation of the hinge to a certain extent to shorten a rotation time of the hinge when the hinge is rotated; and
   a brake to fix the hinge when the rotation of the hinge is finished.

\* \* \* \* \*